United States Patent
Castaneda et al.

(10) Patent No.: US 10,130,407 B2
(45) Date of Patent: *Nov. 20, 2018

(54) HEADLESS BONE COMPRESSION SCREW

(71) Applicant: Biomet Manufacturing, LLC, Warsaw, IN (US)

(72) Inventors: Alfredo Castaneda, Miami, FL (US); Michael Gellatly, Miami Springs, FL (US); Sean Graham, Naples, FL (US)

(73) Assignee: Biomet Manufacturing, LLC, Warsaw, IN (US)

( * ) Notice: Subject to any disclaimer, the term of this patent is extended or adjusted under 35 U.S.C. 154(b) by 205 days.

This patent is subject to a terminal disclaimer.

(21) Appl. No.: 14/993,203

(22) Filed: Jan. 12, 2016

(65) Prior Publication Data

US 2017/0196612 A1    Jul. 13, 2017

(51) Int. Cl.
*A61B 17/86* (2006.01)
*A61B 17/88* (2006.01)
(Continued)

(52) U.S. Cl.
CPC .......... *A61B 17/8645* (2013.01); *A61B 17/84* (2013.01); *A61B 17/863* (2013.01); *A61B 17/864* (2013.01); *A61B 17/8635* (2013.01); *A61B 17/8888* (2013.01); *A61B 2017/564* (2013.01); *A61B 2017/681* (2013.01)

(58) Field of Classification Search
CPC .. A61B 17/8645; A61B 17/84; A61B 17/8888
See application file for complete search history.

(56) References Cited

U.S. PATENT DOCUMENTS 5,403,136 A  *  4/1995  Mathys ............... A61B 17/744
                                                            411/263
5,562,672 A     10/1996  Huebner et al.
(Continued)

FOREIGN PATENT DOCUMENTS

FR         2760628 A1   9/1998
WO   WO-2007109132 A2   9/2007
(Continued)

OTHER PUBLICATIONS

"International Application Serial No. PCT/US2017/013184, Interntional Search Report dated Mar. 24, 2017", 6 pgs.
(Continued)

*Primary Examiner* — Christian Sevilla
(74) *Attorney, Agent, or Firm* — Schwegman Lundberg & Woessner, P.A.

(57) ABSTRACT

Headless compression screws are described. The headless compression screws include first and second ends coupled by a shaft, a first threaded portion positioned proximate the first end that surrounds the shaft and includes s first threads spaced apart from one another at a constant pitch, and a second threaded portion proximate the second end that surrounds the shaft and includes second threads. The second threads are spaced apart from one another at a variable pitch, such that distances between adjacent threads of the second threaded portion decrease as distance from the second end decreases. Methods of reducing a fracture using headless compression screws are also described.

13 Claims, 7 Drawing Sheets

(51) Int. Cl.
  *A61B 17/84* (2006.01)
  *A61B 17/68* (2006.01)
  *A61B 17/56* (2006.01)

(56) References Cited

U.S. PATENT DOCUMENTS

| | | |
|---|---|---|
| 5,871,486 A | 2/1999 | Huebner |
| 5,964,768 A | 10/1999 | Huebner |
| 6,030,162 A | 2/2000 | Huebner |
| 6,984,235 B2 | 1/2006 | Huebner |
| 8,070,786 B2 | 12/2011 | Huebner et al. |
| 8,128,671 B2 | 3/2012 | Taylor |
| 9,161,793 B2 | 10/2015 | Huebner |
| 2013/0211468 A1 | 8/2013 | Huebner |
| 2014/0277190 A1 | 9/2014 | Splieth et al. |
| 2015/0201984 A1* | 7/2015 | Orbay .................. A61B 17/863 606/304 |
| 2017/0196608 A1 | 7/2017 | Castaneda et al. |

FOREIGN PATENT DOCUMENTS

| | | |
|---|---|---|
| WO | WO-2015100149 A1 | 7/2015 |
| WO | WO-2017123753 A1 | 7/2017 |

OTHER PUBLICATIONS

"International Application Serial No. PCT/US2017/013184, Written Opinion dated Mar. 24, 2017", 8 pgs.
"U.S. Appl. No. 15/404,917, Non Final Office Action dated Dec. 4, 2017", 8 pgs.

* cited by examiner

HEADLESS BONE COMPRESSION SCREW

BACKGROUND

One method of reducing a fracture across two bone fragments is driving a compression screw across the fracture site. Some compression screws may have a variable thread pitch along the length of the screw to aid in compressing the fracture. For fractures distal from the surface of the bone, it may be desirable to have a compression screw with no head, such that the screw can be inserted deeply into the bone. One example of such a fracture is a proximal third fracture of the scaphoid. Generally, after the fracture has healed, the compression screw or screws can be removed.

OVERVIEW

The present inventors have recognized, among other things, that a problem to be solved can include the lack of appropriate tactile feedback to surgeons that are implanting certain compression screws. Surgeons can struggle with understanding whether the certain screws have been advanced substantially far enough to fully reduce the fracture, as the torsional resistance experienced by the surgeon turning the compression screw does not correlate to the compression of the bone fragments. Some designs are also not effective enough at providing sufficient compression between the two bone fragments and are difficult to remove after the fracture has been healed. The present subject matter can help provide a solution to this problem, such as by providing a headless compression screw that can include a first threaded portion proximate a first end of the screw that surrounds the shaft and comprises first threads. The first threads can be spaced apart from one another at a constant pitch and a second threaded portion proximate the second end that surrounds the shaft and comprises second threads. The second threads can be spaced apart from one another at a variable pitch, such that distances between adjacent threads of the second threaded portion can decrease as distance from the second end decreases. This construction can aid in creating a correlation between the torsional force and the compression level of the two bone fragments. Additionally, the compression screw can be more easily removed after healing of the fracture than certain other compression screws.

The present description also provides for a method of reducing a fracture between a proximal and distal bone fragment the method. The method can include driving a first end of a headless compression screw through the proximal bone fragment and into the distal bone fragment. The first end can comprise a first threaded portion that can include first threads spaced apart from one another at a constant pitch. A second end of the headless compression screw can be driven through the distal bone fragment, the second end comprising a second threaded portion that includes second threads spaced apart from one another at a varying pitch. The pitch can vary continuously as distance from the second end decreases. Driving the second end through the proximal bone fragment can compress the distal bone fragment and proximal bone fragment together. The torque required to drive the second end through the proximal bone fragment can be correlated to the compressive force between the proximal and distal bone fragments, such that before compression occurs, both the torque and compression are both near zero, and as compression begins to occur, both torque and compression increase in a near linear manner.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
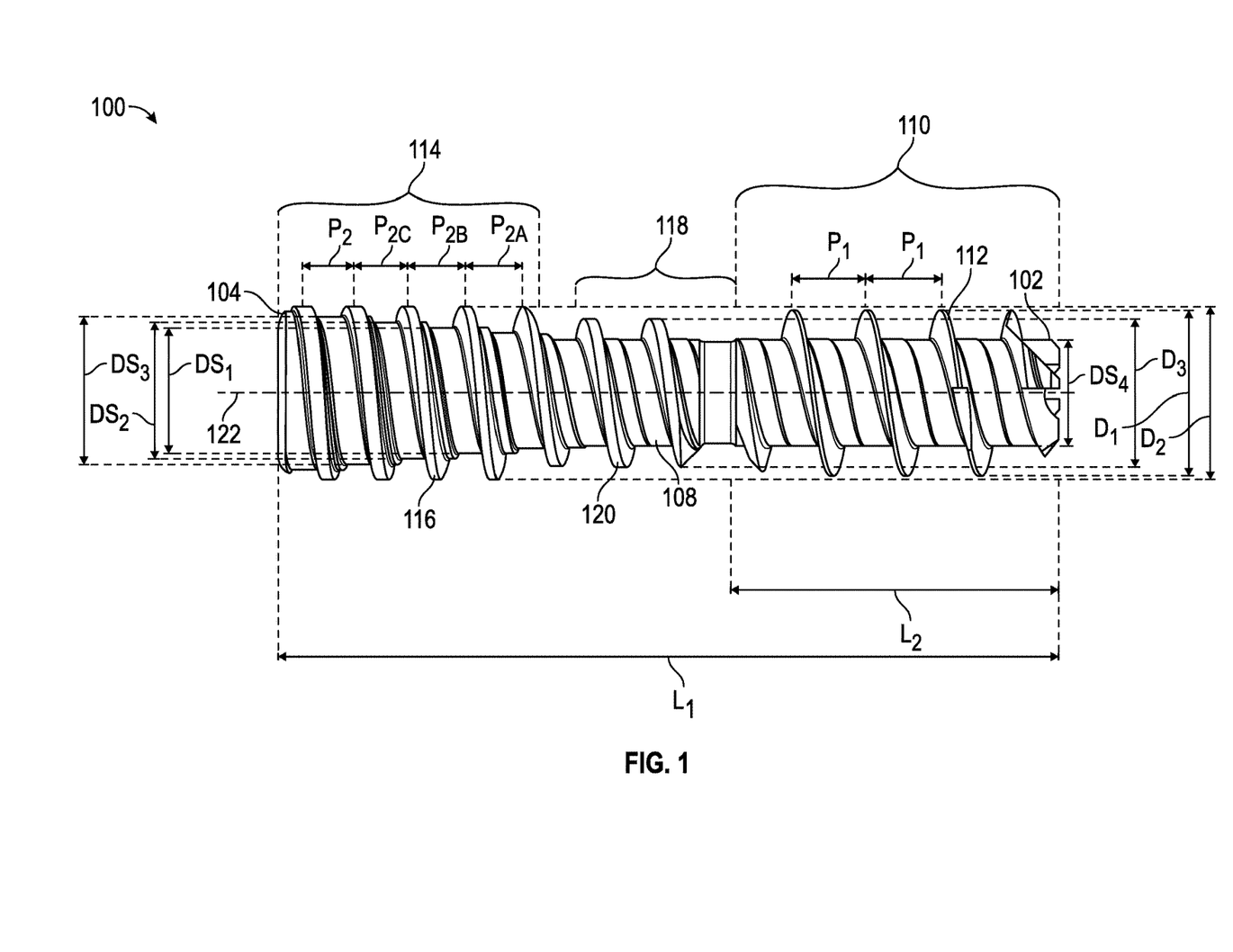
FIG. 1 is a side view of a compression screw according to an example of the present description.
Figure 2:
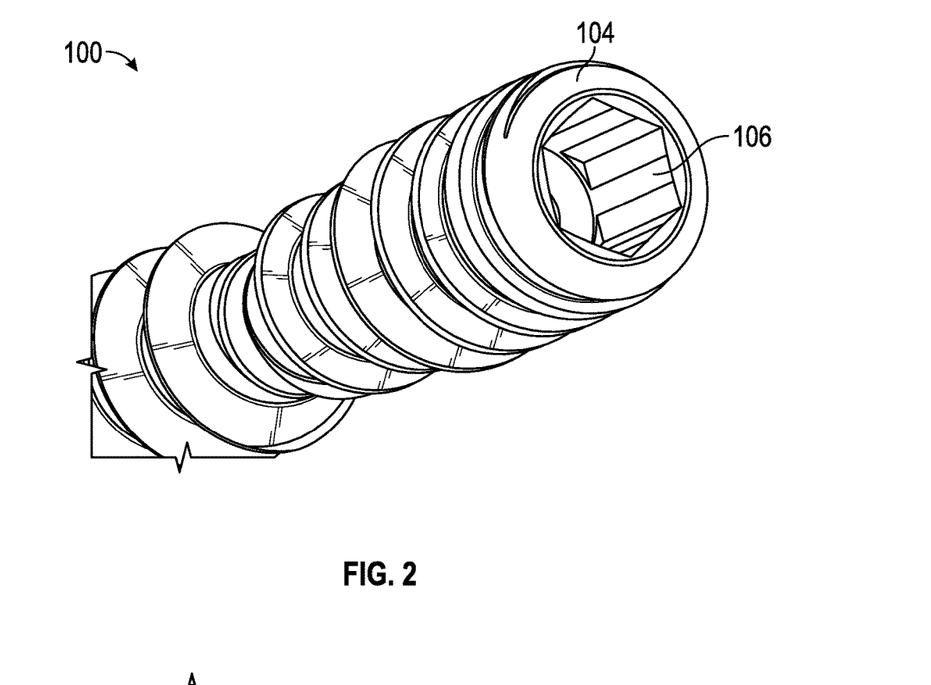
FIG. 2 is a perspective second end view of a compression screw according to an example of the present description.
Figure 3:
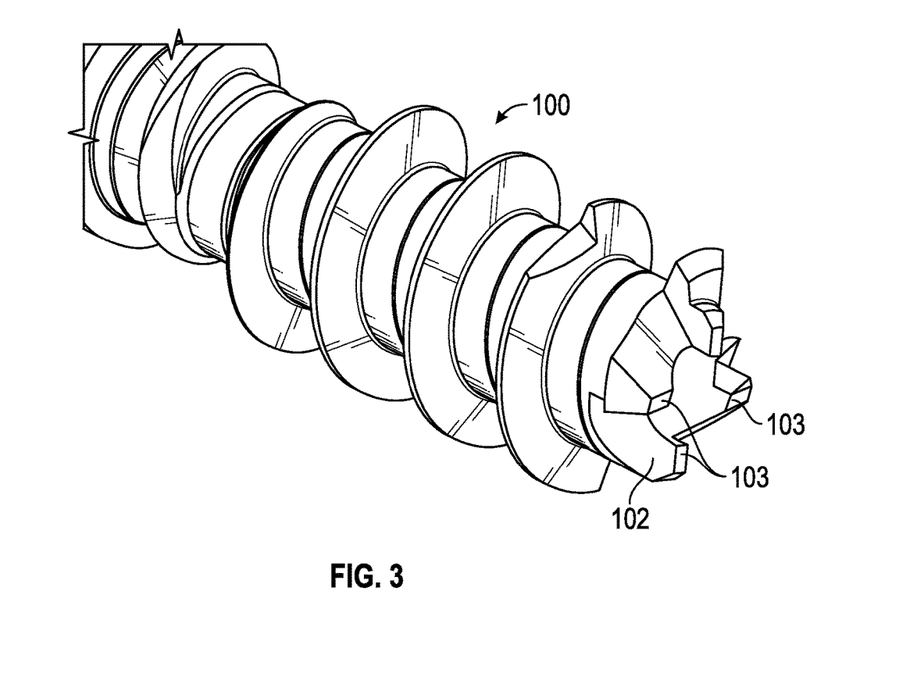
FIG. 3 is a perspective first end view of a compression screw according to an example of the present description.

FIG. 1 illustrates a headless compression screw 100 according to an example in the present description. Headless compression screw 100 can include a first end 102 that is configured for insertion into a bone. Headless compression screw 100 can further include a second end 104 opposite the first end 102. The second end 104 can include a driver engagement feature 106 (e.g., illustrated in FIG. 2). As shown, the driver engagement feature 106 can include a female hexagonal feature formed into the second end 104. However, other shaped features are also contemplated (both male and female). For example, the driver engagement feature 106 can include a cruciate shape, square shape, six-point star shape, or the like. Where a hexagonal (or "hex") feature is used, the headless compression screw 100 can be driven by a driver that can include a male hexagonal engagement portion. The driver can engage the headless compression screw, such as via the female hex feature, and can be capable of driving the headless compression screw across a bone fracture. A perspective view of the second end 102 of headless compression screw 100 is provided in FIG. 3. This view illustrates an example of the flutes 103 present at first end 102 that can aid in the headless compression screw's self-drilling and self-tapping capability. The sharpened nature of the flutes 103 can help assure that a distal bone segment is not "pushed away" when the drill is being inserted through the proximal and then distal bone segments.

Returning to FIG. 1, a shaft 108 connects the first end 102 and second end 104. The headless compression screw 100 can include a first threaded portion 110 that can be located proximate the first end 102. First threaded portion 110 can include first threads 112 that can be spaced apart from one another at a constant pitch, $P_1$. Although described as "threads" 112, it will be understood that the term "threads" may also be understood as a single thread that wraps around shaft 108. The headless compression screw can further include a second threaded portion 114 that can be located proximate the second end 104 and can surround the shaft 108. The second threaded portion includes second threads 116 that can be spaced apart from one another at variable pitch (e.g. $P_{2A}$, $P_{2B}$, $P_{2C}$, etc.). Although described as "threads" 116, it will be understood that threads may also be understood as a single thread that wraps around shaft 108. The distances between adjacent threads 116 of second threaded portion 114 decrease as a distance from the second end 104 decreases (i.e. $P_{2C}<P_{2B}<P_{2A}$, and the like). The largest pitch (e.g. $P_{2A}$) of the second threaded portion 114 can be less than or equal to the constant pitch $P_1$ of the first threaded portion 110. In an example, the pitch $P_2$ of the second threads 116 in second portion 114 can be close to 1.0 mm immediately proximate second end 104 (or between about 0.9 mm and about 1.1 mm), and the pitch $P_2$ of the threads closest to first portion 110 can be close to 1.3 mm (or between about 1.2 mm and about 1.4 mm). The fixed pitch $P_1$ of first threads 112 in first threaded portion can be about 1.5 mm (or between 1.4 mm and about 1.6 mm).

In an example, the first threaded portion 110 and second threaded portion 114 can be directly adjacent to one another (i.e., distanced from each other by no more than a pitch distance of one of the two portions). Or, as shown in FIG. 1, the headless compression screw 100 can further include an intermediate portion 118 that is positioned along the shaft 108 between the first threaded portion 110 and second threaded portion 114. As illustrated, in an example, the intermediate portion 118 can include threads 120 that have an outer diameter $D_3$ that is less than the outer diameter $D_1$ of the threads 112 of first threaded portion 110 and less than the outer diameter $D_2$ of the threads 116 of the second threaded portion 114.

Headless compressions screws described herein can be manufactured using appropriate manufacturing techniques, such as machining. Specifically, the headless compression screws described herein can be manufactured using Swiss machining. The headless compression screws can generally be made of a high strength metal, such as titanium.

Figure 4:
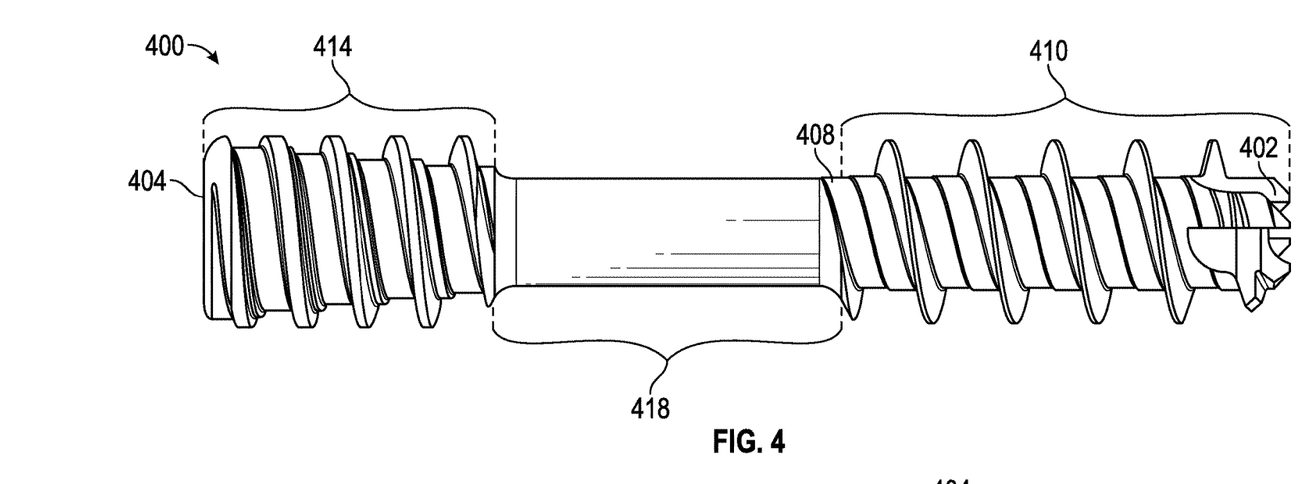
FIG. 4 is a side view of a compression screw according to an example of the present description.
Figure 5:
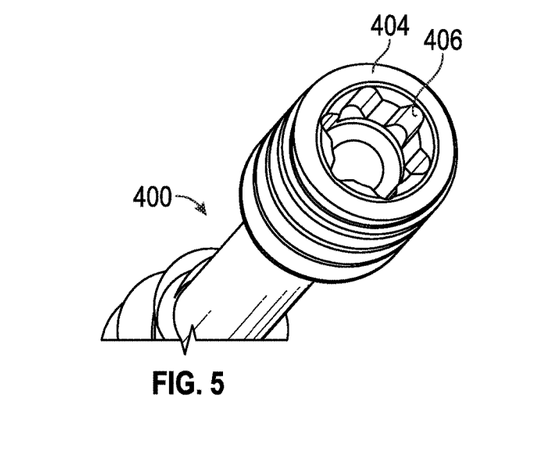
FIG. 5 is a perspective second end view of a compression screw according to an example of the present description.

In an embodiment, illustrated further below, the intermediate portion can be unthreaded. Such an example is provided in FIG. 4. Here, headless compression screw 400 can include a first end 402, an opposing second end 404, and a shaft 408 connecting the first and second ends. The headless compression screw 400 can share many of the same features as compression screw 100, such as a first threaded portion 410 and second threaded portion 414 that may have like characteristics as first threaded portion 110 and second threaded portion 114 of FIG. 1. However, as illustrated, the intermediate portion 418 of the present example is unthreaded. This construction may be beneficial in reducing the amount of bony growth around the intermediate portion 418 of the screw 400 and thus may aid in removal of the headless compression screw 400 after the fracture is healed. In an example, the headless nature of compression screws 100 and 400 can also ease removal and insertion of the screws. Headless compression screw 400 may, similar to the construction shown in FIG. 2, include a hex head for engaging with the driver. As shown in FIG. 5, the second end 404 can include a driver engagement feature 406 that is a female six-point star feature, among other potential shapes.

As further illustrated in FIG. 1, in an example, the diameter of the shaft can decrease in the area of the shaft 108 that corresponds to the second threaded portion 114 as distance from the second end 104 decreases. For instance, $DS_1<DS_2<DS_3$. The decrease may be such that the diameter of the shaft is tapered in the second threaded portion by between 10° and 15°. However, as further illustrated, the diameter $D_2$ of the outermost portion of the second threads 116 in the second threaded portion 114 may remain constant as distance from the second end 104 increases. In an example, in the first threaded portion 110, the diameter of the shaft $DS_4$ and the outermost portion of the first threads 114, $D_1$, remain constant throughout the first threaded portion 110.

The headless compression screw 100 can have a length $L_1$ along the longitudinal axis 122 of the screw 100 and the first threaded portion 110 can have a length $L_2$ along the longitudinal axis 122. The present inventors have discovered that an appropriate ratio of the length of the first threaded portion 110 to the entire compression screw 100 can provide unique advantages. In an example, the first threaded portion 110 has a length $L_2$ that is between about 30% and about 50% of the length $L_1$ of the headless compression screw 100. Further, the first threaded portion 110 can have a length $L_2$ that is between about 35% and about 45% of the length $L_1$ of the headless compression screw 100, or a ratio of length $L_2$ that is between about 38% and about 42% of the length $L_1$. In an example, the ratio of $L_2$ to $L_1$ can be approximately 40%. The provided ratios can aid in providing a linear or near-linear torque to compression relationship, such as described further below.

Figure 6:
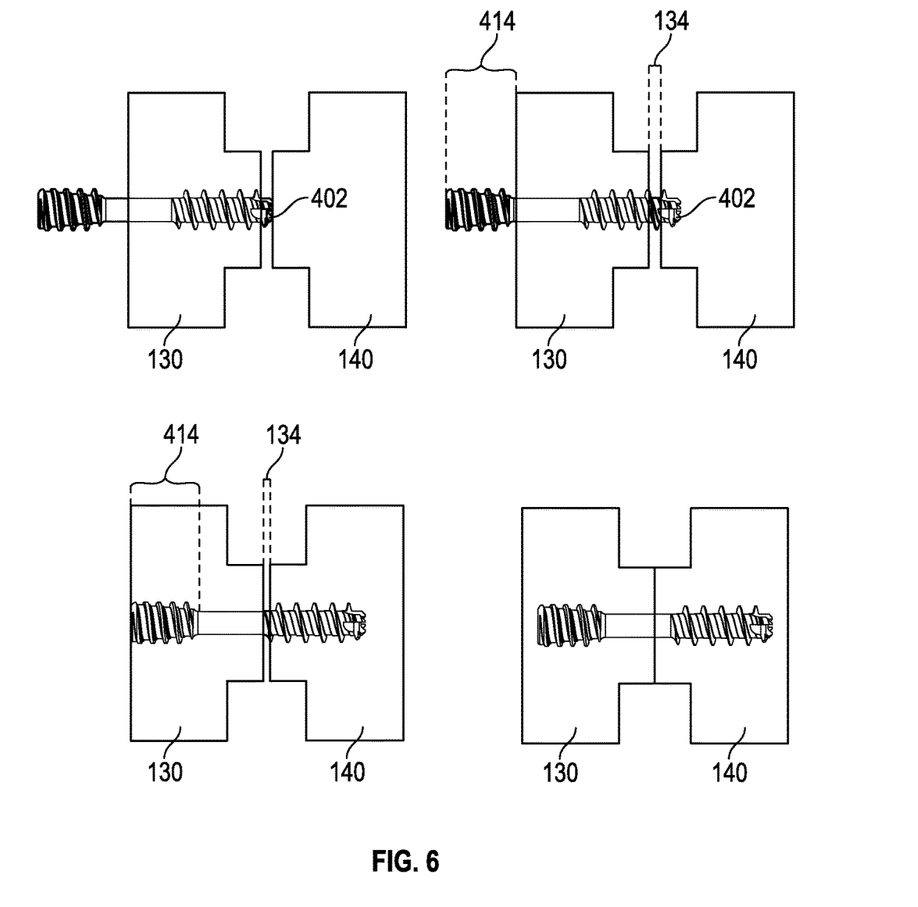
FIG. 6 illustrates a side view of a compression screw reducing a fracture at various points in a procedure.

In an example, the headless compression screw 400 is configured to reduce a fracture 134. An example of such a reduction (in various points in the procedure) is illustrated in FIG. 6. The first end 402 of the headless compression screw is configured to enter and travel through a proximal bone fragment 130 and enter a distal bone fragment 140. As further illustrated in FIG. 6, driving the second portion 414 through the proximal bone fragment 130 compresses the proximal bone fragment 130 and distal bone fragment 140 towards one another, compressing the fracture 134, until the fracture 134 is completely reduced and the proximal bone fragment 130 and distal bone fragment are compressed against one another. The headless compression screw 400 used in such a method can exhibit desirable tactile feedback qualities to the surgeon driving the screw. Specifically, the compression level between the proximal bone fragment 130 and distal bone fragment and the torque experienced by a driver that drives the compression screw 400 each linearly increase from at or close to zero as the second portion drives through the proximal bone fragment.

Figure 7:
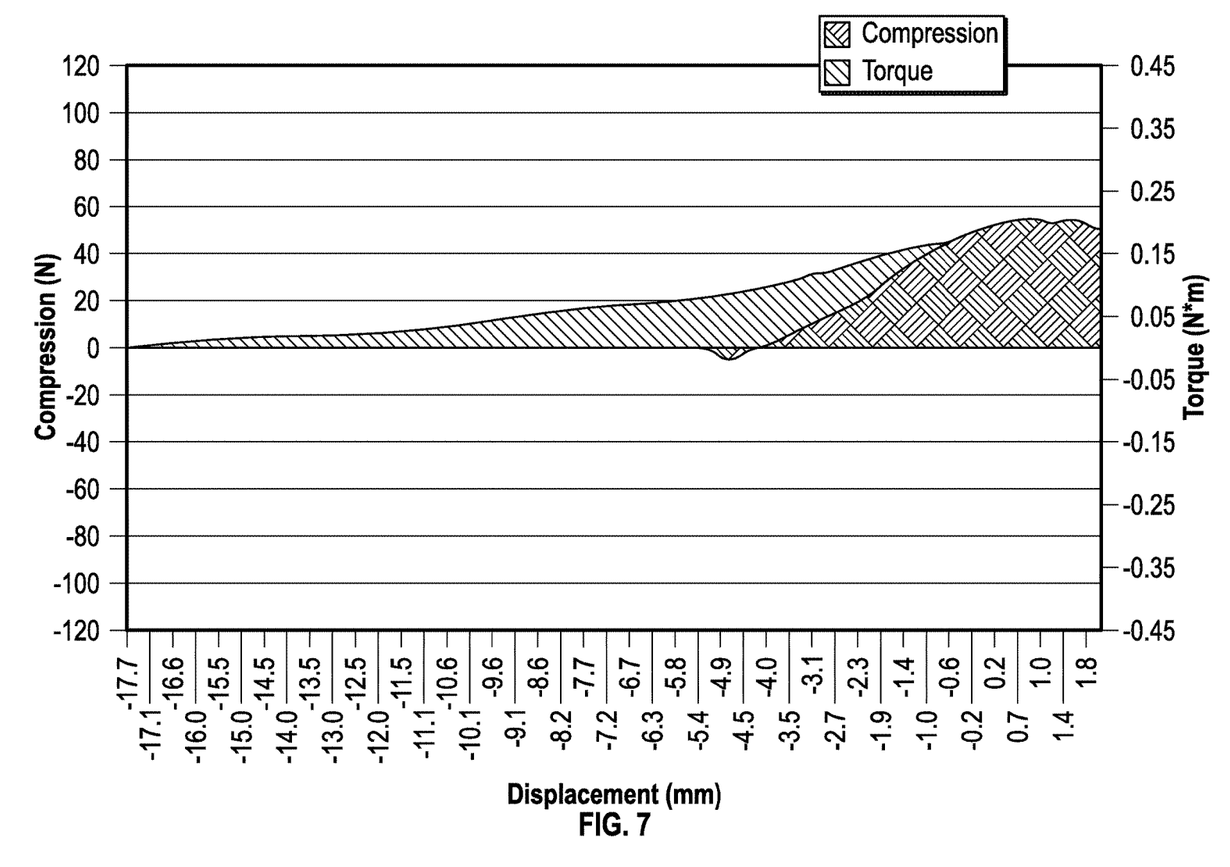
FIG. 7 is a graph of compression of fracture vs. torque experienced for a known compression screw.
Figure 8:
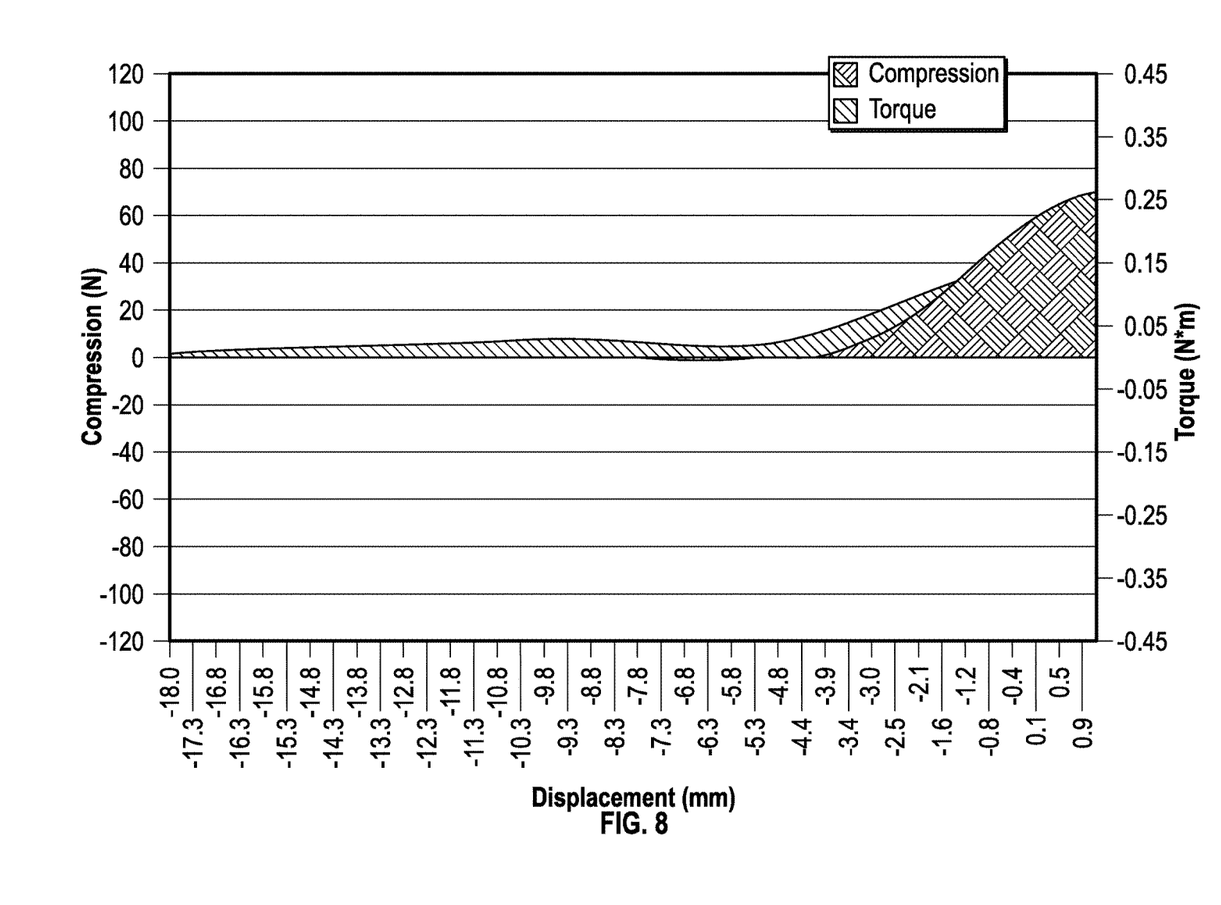
FIG. 8 is a graph of compression of fracture vs. torque experienced for a headless compression screw according to one example of the present description.

A graph illustrating the relationship of compression vs. torque force experienced by the driver of another currently used compression screw is illustrated in FIG. 7 and a graph of the compression vs. torque relationship of the presently described screw is presented in FIG. 8. As illustrated in FIG. 7, in the currently used compression screw the amount of torque experienced generally linearly increases from the point where a first end of the compression screw is inserted into a proximal bone fragment (far left of graph) until the fracture has been fully reduced (i.e. it increases across the entirety of the insertion of the screw—far right of graph). As such, it is not clear to the surgeon driving the screw when compression of the fracture is occurring. In contrast, as shown in FIG. 8 the torque experienced by the presently described headless compression screw is minimal (near zero) and nearly constant from the point that the first end of the compression screw enters the proximal bone fragment (far left of graph), past the point that the first end enters the distal fragment, until the second threaded portion (e.g. 114) of the compression screw enters the distal fragment. At that point the torque experienced by the driver begins to increase in a generally linear manner, and the compression of the fracture also begins to occur in a near linear manner. Thus, the surgeon can better sense that compression has begun and that he or she needs to be sensitive to further advancement. At a given threshold of torque experienced, the surgeon will be aware that the fracture has been fully reduced and that he or she should stop driving the compression screw. As such the torque experienced vs. compression achieved are correlated.

Figure 9:
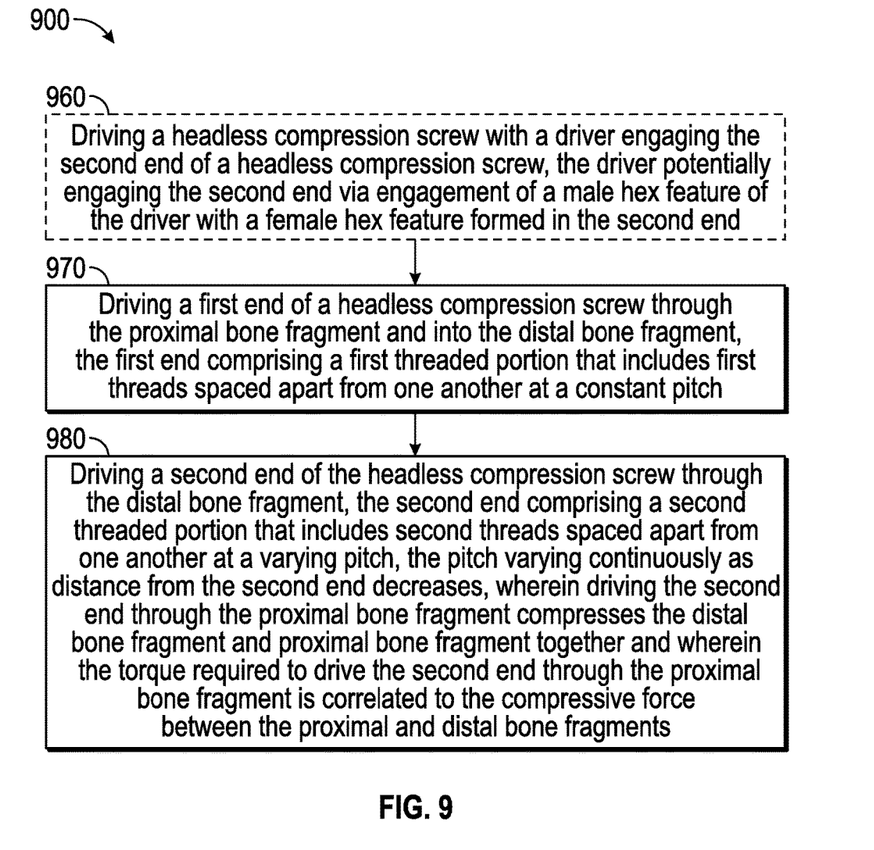
FIG. 9 is a block diagram of a method of reducing a fracture between a proximal and distal bone fragment according to one example of the present description.

FIG. 9 provides a block diagram of a potential method of inserting a headless compression screw such as described in the present description. As illustrated, the method can include driving a first end of a headless compression screw through the proximal bone fragment and into the distal bone fragment (process 970). The first end can include a first threaded portion that includes first threads spaced apart from one another at a constant pitch. The method further can include driving a second end of the headless compression screw through the distal bone fragment (process 980). The second end can include a second threaded portion that includes second threads spaced apart from one another at a varying pitch, where the pitch varies continuously as distance from the second end decreases. Driving the second end through the proximal bone fragment can compress the distal bone fragment and proximal bone fragment together, and the torque required to drive the second end through the proximal bone fragment will be generally correlated to the compressive force between the proximal and distal bone fragments. As further illustrated in FIG. 9, optionally, the method can include driving the headless compression screw with a driver that engages with the second end of the headless compression screw (process 960). In one example, the driver engages the second end of the headless compression screw via engagement of a first male hex feature on the end of the driver with a female hex features formed into the second end. As noted above, other appropriate male and female features are contemplated for the second end of the headless compression screw (e.g. a cruciate shape, square shape, six-point star shape and the like).

VARIOUS NOTES & EXAMPLES

Example 1 is a headless compression screw, comprising: a first end configured for insertion into a bone; a second end opposite the first end, the second end comprising a driver engagement feature; a shaft connecting the first end and second end; a first threaded portion proximate the first end that surrounds the shaft and comprises first threads, the first threads being spaced apart from one another at a constant pitch; a second threaded portion proximate the second end that surrounds the shaft and comprises second threads, the second threads being spaced apart from one another at a variable pitch, such that distances between adjacent threads of the second threaded portion decrease as distance from the second end decreases.

Example 2 can include, or can optionally be combined with the subject matter of Example 1 to optionally include wherein the first threaded portion and second threaded portions are directly adjacent to one another.

Example 3 can include, or can optionally be combined with the subject matter of any one or more of Examples 1-2 to optionally include further comprising an intermediate portion positioned along the shaft between the first threaded portion and second threaded portion.

Example 4 can include, or can optionally be combined with the subject matter of Example 3 to optionally include wherein the intermediate portion is unthreaded.

Example 5 can include, or can optionally be combined with the subject matter of any one or more of Examples 3-4 to optionally include wherein the intermediate portion comprises threads having an outer diameter less than an outer diameter of the threads of the first and second portions.

Example 6 can include, or can optionally be combined with the subject matter of any one or more of Examples 1-5 to optionally include wherein the diameter of the shaft decreases in the area of the shaft that corresponds to the second threaded portion as the distance from the second end increases.

Example 7 can include, or can optionally be combined with the subject matter of any one or more of Examples 1-6 to optionally include wherein the diameter of the outermost portion of second threads in the second threaded portion remain constant as distance from the second end increases.

Example 8 can include, or can optionally be combined with the subject matter of any one or more of Examples 1-7 to optionally include wherein the diameters of the shaft and the outermost portion of the first threads in the first threaded portion remain constant throughout the first threaded portion.

Example 9 can include, or can optionally be combined with the subject matter of any one or more of Examples 1-8 to optionally include wherein the first threaded portion comprises a length that is between about 30% and about 50% of a length of the headless compression screw.

PNUM In Example 10 can include, or can optionally be combined with the subject matter of any one or more of Examples 1-9 to optionally include wherein the first threaded portion comprises a length that is between about 35% and about 45% of a length of the headless compression screw.

Example 11 can include, or can optionally be combined with the subject matter of any one or more of Examples 1-10 to optionally include wherein a largest pitch of the second threaded portion is less than or equal to the constant pitch of the first threaded portion.

Example 12 can include, or can optionally be combined with the subject matter of any one or more of Examples 1-11 to optionally include wherein the driver engagement feature comprises a female hex feature formed into the second end.

Example 13 is a system comprising: the headless compression screw of Example 12; and a driver comprising a male hexagonal engagement portion can include, or can optionally be combined with the driver engaging the headless compression screw via the female hex feature and capable of driving the headless compression screw across a bone fracture.

Example 14 can include, or can optionally be combined with the subject matter of any one or more of Examples 1-13 to optionally include wherein the screw is configured to reduce a fracture, and wherein the first end is configured to travel through a proximal bone fragment and enter a distal bone fragment.

Example 15 can include, or can optionally be combined with the subject matter of Example 14 to optionally include wherein driving the second portion through the proximal bone fragment compresses the proximal bone fragment and distal bone fragment towards each other.

Example 16 can include, or can optionally be combined with the subject matter of Example 15 to optionally include wherein the compression level between proximal bone fragment and distal bone fragment is generally linearly correlated to torque experienced by a driver that drives the compression screw.

Example 17 is a method of reducing a fracture between a proximal and distal bone fragment the method comprising: driving a first end of a headless compression screw through the proximal bone fragment and into the distal bone fragment, the first end comprising a first threaded portion that includes first threads spaced apart from one another at a constant pitch, and driving a second end of the headless compression screw through the distal bone fragment, the second end comprising a second threaded portion that includes second threads spaced apart from one another at a varying pitch, the pitch varying continuously as distance from the second end decreases, wherein driving the second end through the proximal bone fragment compresses the distal bone fragment and proximal bone fragment together, and wherein the torque required to drive the second end through the proximal bone fragment is linearly correlated to the compressive force between the proximal and distal bone fragments.

Example 18 can include, or can optionally be combined with the subject matter of Example 17 to optionally include wherein the method further comprises driving with headless compression screw with a driver that engages with the second end of the headless compression screw.

Example 19 can include, or can optionally be combined with the subject matter of any one or more of Examples 17-18 to optionally include wherein a driver engages the second end of the headless compression screw via engagement of a first male hex feature on the end of the driver with a female hex features formed into the second end.

Example 20 can include, or can optionally be combined with the subject matter of any one or more of Examples 17-19 to optionally include wherein the headless compression screw comprises an intermediate portion between the first and second threaded portions, the intermediate portion being unthreaded or including threads of a diameter less than the threads of the first and second threads.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:
1. A headless compression screw, comprising:
a shaft extending from a first end to a second end, the first end configured for insertion into a bone, and the second end comprising a driver engagement feature, the shaft comprising:
  a first threaded portion proximate the first end and comprising a first thread, the first thread extending along the first threaded portion at a constant pitch;
  a second threaded portion proximate the second end and comprising a second thread that is separate from the first thread, the second thread extending along the second threaded portion at a variable pitch such that distance between adjacent turns of the second thread decrease as distance from the second end decreases, wherein a diameter of the shaft decreases and a height of the second thread increases to maintain a constant outer diameter of the second thread across a length of the shaft that corresponds to the second threaded portion as the distance from the second end increases, wherein the largest pitch of the varying pitch is less than or equal to the constant pitch of the first thread, wherein the second threaded portion reduces and compresses a proximal and a distal bone fragment engaged by the headless compression screw, and wherein the second threaded portion is configured to provide tactile feedback to a user indicative of the compression applied to the proximal bone fragment and the distal bone fragment; and an intermediate portion positioned along the shaft between the first threaded portion and the second threaded portion.

2. The headless compression screw of claim 1, wherein the intermediate portion is unthreaded.

3. The headless compression screw of claim 1, wherein the intermediate portion comprises a third thread having an outer diameter that is less than an outer diameter of the first thread and the second thread.

4. The headless compression screw of claim 1, wherein a diameter of the shaft and an outermost portion of the first thread remains constant across a length of the first threaded portion.

5. The headless compression screw of claim 1, wherein the first threaded portion comprises a length that is between about 30% and about 50% of a length of the headless compression screw.

6. The headless compression screw of claim 1, wherein the first threaded portion comprises a length that is between about 35% and about 45% of a length of the headless compression screw.

7. The headless compression screw of claim 1, wherein a largest pitch of the second threaded portion is less than or equal to the constant pitch of the first threaded portion.

8. The headless compression screw of claim 1, wherein the driver engagement feature comprises a female hex feature disposed in the second end.

9. A system comprising: the headless compression screw of claim 8; and a driver comprising a male hexagonal engagement portion, the driver engaging the headless compression screw via the female hex feature and capable of driving the headless compression screw across a bone fracture.

10. A method of reducing a fracture between a proximal and distal bone fragment, the method comprising:

driving a first end of a headless compression screw through the proximal bone fragment and into the distal bone fragment, the first end comprising a first threaded portion that includes a first thread extending along the first threaded portion at a constant pitch;

driving an intermediate region of the headless compression screw through the proximal bone fragment and at least partially into the distal bone fragment; and driving a second threaded portion of a second end of the headless compression screw into the proximal bone fragment to reduce and compress the proximal bone fragment and distal bone fragment and provide tactile feedback to a user indicative of the compression applied to the proximal bone fragment and the distal bone fragment, the second threaded portion including a second thread separate from the first thread extending therealong at a varying pitch such that the distance between adjacent turns of the second thread decrease as distance from the second end decreases, wherein a diameter of the shaft decreases and a height of the second thread increases to maintain a constant outer diameter of the second thread across a length of the shaft that corresponds to the second threaded portion as the distance from the second end increases, and wherein the largest pitch of the varying pitch is less than or equal to the constant pitch of the first thread.

11. The method of claim 10, wherein a driver engages the second end of the headless compression screw via engagement of a first male hex feature on the end of the driver with a female hex features disposed in the second end.

12. The method of claim 10, wherein the intermediate portion is unthreaded.

13. The method of claim 10, wherein the intermediate portion comprises a third thread having an outer diameter that is less than an outer diameter of the first thread and the second thread.

* * * * *

UNITED STATES PATENT AND TRADEMARK OFFICE
CERTIFICATE OF CORRECTION

PATENT NO. : 10,130,407 B2
APPLICATION NO. : 14/993203
DATED : November 20, 2018
INVENTOR(S) : Castaneda et al.

It is certified that error appears in the above-identified patent and that said Letters Patent is hereby corrected as shown below:

On the Title Page

In Column 2, under "Other Publications", Line 1, delete "Interntional" and insert --International-- therefor In item (57), in "Abstract", in Column 2, Line 4, after "includes", delete "s"

Signed and Sealed this
Twenty-sixth Day of March, 2019

Andrei Iancu
*Director of the United States Patent and Trademark Office*